Figure 1:
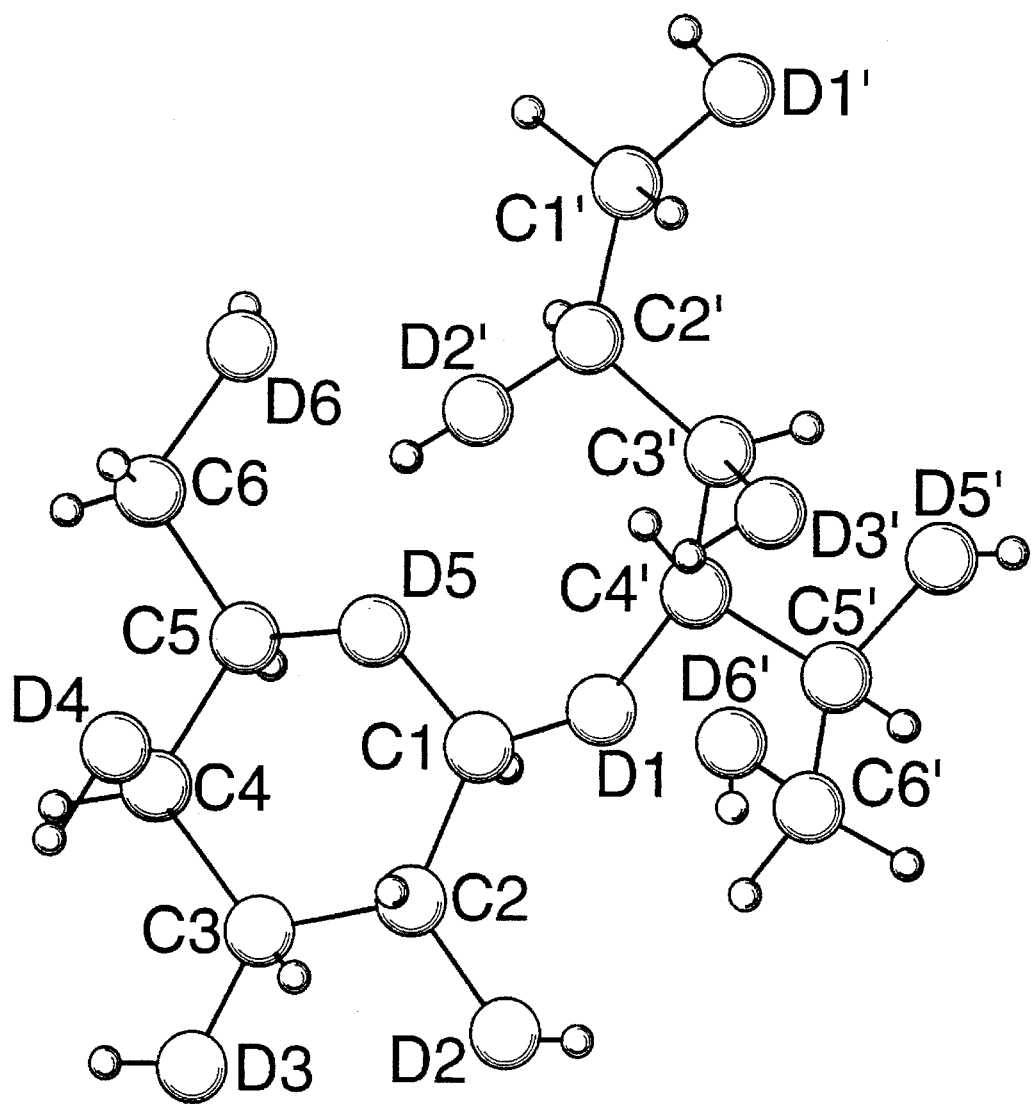

United States Patent [19]

Heikkila et al.

[11] Patent Number: 5,494,525
[45] Date of Patent: Feb. 27, 1996

[54] CRYSTALLINE ANHYDROUS LACTITOL AND A PROCESS FOR THE PREPARATION THEREOF AS WELL AS USE THEREOF

[75] Inventors: Heikki O. Heikkila, Espoo; Juha V. Nurmi, Pinjainen, both of Finland; Tammy Pepper, Weybridge, Great Britain

[73] Assignee: Xyrofin OY, Helsinki, Finland

[21] Appl. No.: 122,423

[22] PCT Filed: Mar. 19, 1992

[86] PCT No.: PCT/FI92/00077

§ 371 Date: Jan. 6, 1994

§ 102(e) Date: Jan. 6, 1994

[87] PCT Pub. No.: WO92/16542

PCT Pub. Date: Jan. 10, 1992

[30] Foreign Application Priority Data

Mar. 22, 1991 [FI] Finland ................. 911411

[51] Int. Cl.⁶ ............. C13F 32/00; C13K 5/00; A61K 31/715; C07H 1/00

[52] U.S. Cl. ............. 127/61; 127/30; 127/31; 514/53; 514/777; 536/1.11; 536/127

[58] Field of Search ............. 127/61, 30, 31; 514/53, 777; 536/1.11, 127

[56] References Cited

U.S. PATENT DOCUMENTS

| | | | |
|---|---|---|---|
| 3,973,050 | 8/1976 | Hayashibara et al. | 426/552 |
| 4,216,025 | 8/1980 | Monti | 127/61 |
| 5,160,546 | 11/1992 | Kawashima et al. | 127/60 |
| 5,162,517 | 11/1992 | Darsow | 536/124 |

FOREIGN PATENT DOCUMENTS

| | | | |
|---|---|---|---|
| 0039981 | 11/1981 | European Pat. Off. | |
| WO9006317 | 6/1990 | WIPO | C07H 15/04 |

OTHER PUBLICATIONS

STN International File CA, Chemical Abstracts, vol. 114, No. 7, 18 Feb. 1991 (Columbus, Ohio, US), Kawashima Shigeru, et al: "Manufacture of lactitol anhydrate crystals and crystal compositions containing lactitol anhydrate", abstract no. 60708u, & JP 02255694 A2 16 Oct. 1990, JP 89–75204 29 Mar. 1989.

Trans. Faraday Soc., vol. 24, 1928 M. L. Wolfrom et al.: "Crystalline lactositol", see p. 571–p. 573 Mar. 1938.

STN International, file CA, Chemical Abstracts vol. 114, No. 5, 4 Feb. 1991, (Columbus, Ohio, US) Kawashima Shigeru et al: "Novel lactitol anhydrate crystals, raw sugars crystals containing them, and their manufacture", abstract No. 41308x, & JP 02200695 A2 8 Aug. 1990, JP 89–19452 31 Jan. 1989.

Primary Examiner—Paul Lieberman
Assistant Examiner—Patricia L. Hailey
Attorney, Agent, or Firm—Kenyon & Kenyon

[57] ABSTRACT

The invention relates to a novel crystalline anhydrous lactitol, a process for the preparation thereof, and the use thereof. The novel crystalline anhydrous lactitol belongs to the monoclinic crystal system and has the unit cell constants: (a)= 7.614 A; (b)=10.757 A; (c)=9.370 A and β=108.2°. Its melting point is between 149° C. and 152° C., water content below 0.5% and lactitol content more than 99%; it has a low hygroscopicity.

7 Claims, 1 Drawing Sheet

CRYSTALLINE ANHYDROUS LACTITOL AND A PROCESS FOR THE PREPARATION THEREOF AS WELL AS USE THEREOF

The present invention relates to a novel crystalline anhydrous lactitol and a process for the preparation thereof by crystallization from an aqueous solution, and the use thereof.

Lactitol is a special sweetener replacing saccharose; however, its energy content is only half of that of saccharose, and it does not cause an elevated blood glucose content; furthermore, it is friendly to the teeth (cf. Developments in Sweeteners, Ed. Grenby, T. H., Vol. 3, 1987, pp. 65–81).

The preparation of lactitol from lactose has long been known. Industrially lactitol is prepared analogously with the preparation of sorbitol, by hydrogenation in the presence of a Raney nickel catalyst. An aqueous solution of lactose, typically having a concentration of 30% to 40% by weight on account of the low solubility of lactose, is hydrogenated at 70° C. to 130° C. at a pressure of 30 atm to 74 arm. The preparation has been described by Wolfrom, M. L., Burke, W. J., Brown, K. R. and Rose, R. S., J. Am. Chem. Soc. 60 (1938), pp. 571–573.

Crystalline lactitol has been reported to occur in anhydrous form (anhydride) as well as in the form of monohydrate, dihydrate and trihydrate, which have all been known for a long time with the exception of pure monohydrate and Trihydrate. Among the crystal forms of lactitol, lactitol monohydrate is of great commercial interest e.g. on account of its low hygroscopicity.

In accordance with the above-stated reference (Wolfrom et al., 1938), "lactitol anhydride" could be crystallized by adding ethanol to a lactitol solution evaporated to a high concentration. After a crystallization time of one month (from anhydrous ethanol), the lactitol yield was 80%; the product was recrystallized from a water-ethanol solution in an ice bath. The resultant "lactitol anhydride" was a highly hygroscopic substance. The crystal form was tetraedric, the melting point was 144° C. to 146° C. and the specific rotation in water +14° (4 g/100 ml, 23° C.).

In J. Am. Chem. Soc. 74 (1952), p. 1105, Wolfrom et al. state the above "lactitol anhydride" to be metastable, since in renewed tests carried out at two different laboratories only dihydrate was crystallized, having a melting point of 72.5° C. to 74° C. On the basis of the studies presently conducted, the product disclosed by Wolfrom et al. (1938) was an impure dihydrate and not crystalline anhydrous lactitol. The dihydrate prepared by Wolfrom et al. was found to have been anhydrated in the melting point determination, as has been shown in the reference example set out hereinbelow. Therein dihydrate turns into a powdery anhydride below 70° C. when the melting point measurement is started at room temperature, and then melts at about 146° C.

Lactitol hydrate powders anhydrated to a water content below 3% have been prepared by drying both a lactitol solution and crystalline hydrate. The hygroscopicity of these powders is made use of in the drying of moist mixtures (European Patent Application No. 0231643, 1986).

Japanese Patent Application No. 64-19452 (1989) discloses "lactitol anhydride" which is prepared by drying crystalline lactitol monohydrate. The product is hygroscopic and has a melting point of 121° C. to 123° C.

The crystalline anhydrous lactitol of the invention is prepared by crystallizing from an aqueous solution having a lactitol content of more than 70%, preferably more than 90%, on dry solids and having a dry solids content of 80% to 95% by weight, preferably about 90% by weight, in the temperature range 70°–100° C. The crystallization is advantageously carried out by first evaporating, optionally seeding, followed by cooling from about 95° C. to about 80° C., whereafter the crystals are separated from the mother liquor and washed and dried, if necessary.

According to another preferred method, the lactitol solution is evaporated under stirring at a temperature of 80° C. to 90° C., seed crystals are added if desired, and the evaporation is continued, advantageously with addition of solution, to increase the crystal concentration to a dry solids content of about 90% by weight. Thereafter the crystals can be separated and dried, even though it is advantageous to continue the crystallization by cooling the mixture first at a slow rate and ultimately at a faster rate to a temperature of 70° C. to 90° C. until the crystallization yield is appropriate, typically 40% to 60%, whereupon the crystals are separated and, if necessary, washed and dried. Dried crystals are typically obtained at a yield of 30% to 50%, and the purity of the crystals is typically more than 99% and the water content typically below 0.5%. For instance conventional evaporating and cooling crystallizers, centrifuges, and driers of the sugar industry may be used in the preparation.

The crystalline anhydrous lactitol of the invention has a low hygroscopicity; it absorbs less than 0.1% of water in one month when the relative humidity of the ambient air varies in the range 25% to 60% and the temperature in the range 24° C. to 30° C.; at a relative humidity of about 70% and at 20° C. it turns into lactitol monohydrate in about two weeks.

The new crystalline anhydrous lactitol ($C_{12}H_{24}O_{11}$) belongs to the monoclinic crystal system; spatial group $P2_1$; the unit cell parameters are a=7.614 Å, b= 10.757 Å, c=9.370 Å and β=108.2°; the unit cell comprises two molecules and its volume is 729.0 Å$^3$; the calculated density is 1.568 g/cm$^3$. The spatial structure of the crystal is shown in FIG. 1. Its melting point is 149° C. to 152° C., measured by the European Pharmacopoeia method. By measuring the energy absorption maximum with a DSC apparatus and extrapolating the heating rate to be zero, a melting point value of 146° C. to 148° C. is obtained; by measuring with a DSC apparatus (heating rate 2° C./min.) a strong endothermic peak is detected at 151° C.

In connection with this invention, the term crystalline signifies the fact that the product is crystalline in the technical sense (integral crystal structure) and not powdery (microcrystalline). The crystal size of the industrially manufactured product is preferably between 0.2 mm and 0.6 mm depending on the application, and the desired size is obtained when the conventional seeding technique is employed in the crystallization.

The new crystalline anhydrous lactitol has a good flowability and storability, since it is stable at room temperatures, the relative humidity being below 60%. Lactitol stored more than two years under varying room air conditions had a flowability of 7 s/ 100 g measured by the funnel technique, the inclination of the funnel being 60°, the length of the tube 23 mm and the inner diameter 9 mm.

The new crystalline anhydrous lactitol dissolves rapidly in water; the solubility at 25° C. is about 190 g/100 ml of water. Its specific rotation in water is about +14.7° (10 g/100 ml, 20° C.).

On account of its excellent technical and physiological properties, the new crystalline anhydrous lactitol is particularly suitable as a substitute for sugar in foodstuffs and sweets. By combining the new lactitol with other sweeteners, such as saccharine or xylitol, a sweetener resembling sugar and yet having a considerably lower energy content and, furthermore, being friendly to The teeth can be prepared; it can be used instead of sugar for instance in sweets, jams, bakery products, chocolate, juices, chewing gum and ice-creams, as well as in pharmaceutical and hygienic products, such as toothpaste. The new anhydrous lactitol is particularly suitable for the production of chocolate, to which it is considerably better suited than lactitol monohydrate and lactitol dihydrate and anhydrides prepared therefrom by drying.

EXAMPLE 1

Combined evaporation and cooling crystallization 12 kg of lactitol monohydrate produced in the third crystallization step (from the mother liquor obtained from the second step) by The process of PCT Patent Application No. FI89/00142 and having 99% of lactitol on dry solids was dissolved in water to give a solution of about 50% by weight. A quantity of the solution was transferred into an evaporator (20 l rotating evaporator), and the temperature was raised to 80° C. The solution was evaporated under simultaneous stirring, whereupon the lactitol was seeded spontaneously at about 80° C., and thereafter intake of more feed solution into the evaporator was started and the evaporation was continued until the dry solids content was 92.6% by weight.

The resultant mixture containing crystals was transferred into a 10 l cooling crystallizer having a temperature of 92° C. After stirring of about one hour, the mixture was cooled controlledly [$T=92°$ C.$- 4(t/18)^{2°}$ C., wherein T is the temperature and t the time elapsed (hours)]. The crystallization was terminated after cooling of 18 hours at 78° C., at which point the dry solids content of the mother liquor was 83.2% by weight, in other words, the yield was about 60%. The crystals were separated from the mother liquor with a conventional centrifuge (diameter of basket 0.4 m); the centrifuging was carried out for three minutes at a speed of rotation of 1800 rpm. The crystals were washed with 0.5 l of hot water at a speed of rotation of about 1000 rpm. Finally, the crystals were dried with a conventional drum drier with hot air (90° C.). 4.3 kg of dried crystals was obtained (yield about 46%); crystal size about 0.5 mm, melting point 149° C. to 152° C., lactitol content about 99.5%, water content 0.05% and specific rotation in water +14.7° (10 g/100 ml, 20° C.).

EXAMPLE 2

Cooling crystallization

Lactose was hydrogenated in an aqueous solution by the conventional technique. The resultant lactitol solution containing 98.5% of lactitol on dry solids was evaporated to a concentration of 91.5% by weight at a temperature of about 90° C., and 7.7 kg thereof was transferred into a 10 l cooling crystallizer. The crystallizer was a conventional horizontal cylindrical batch-operated cooling crystallizer provided with a mixer and a recycling water jacket whose temperature was controlled by means of a microprocessor.

The cooling of the syrup was started at a rate of 10° C./16 hours, in which connection crystals started to form already after 1.8 hours under stirring. When the temperature was 80° C. (after about 20 hours), the degree of crystallization was found to be good. The crystals were centrifuged off, washed rapidly with water, and dried with a fluidization drier with air having a temperature of about 65° C. Dried crystals were obtained at a yield of about 30%; the crystal size was about 0.45 mm, the melting point 149° C. To 152° C., the lactitol content about 99.5%, water content 0.2% and specific rotation in water +14.7° (10 g/100 ml, 20° C.).

Crystallization examples 1 and 2 are intended to illustrate the practicability of the novel process, but the crystallizations may also be carried out by modifying them in a manner as required by normal effective production operation. Thus the crystallization may also be effected in several steps, in which event a better yield is obtained. The crystallizations may also be carried out in a continuous operation as long as one remains in the temperature range 70°–100° C. and the supersaturation of the mother liquor is maintained appropriate. The seeding may be performed either spontaneously or preferably by adding seed crystals, whereby the crystal size of the product can be predetermined.

EXAMPLE 3

Seeded evaporation and cooling crystallization

A lactitol solution (the same as in test 2) was evaporated in a 400 l pilot crystallizer in the temperature range 75°–80° C., simultaneously adding new solution. The crystallizer had the construction of a typical sugar crystallizer. When the dry solids content of the solution was about 88% by weight and the temperature 80° C., 4 g of finely ground seed crystals obtained from Example 2 was added. The evaporation was continued further for one hour at 80° C. simultaneously feeding new solution, at which point the crystal content was found to be suitable, and the mixture was transferred to a 400 l cooling crystallizer (of a construction similar to that used in Example 2) having a temperature of 80° C. The temperature of the mixture was lowered linearly in 17 hours to 70° C. under simultaneous stirring, at which point the crystal content was sufficient. The crystals were centrifuged off, washed rapidly with water, and dried in a drum drier with air having a temperature of about 80° C. Dried crystals were obtained at a yield of about 35%; the crystal size was about 0.30 mm, melting point from 149° C. to 151° C., lactitol content about 9.5% and water content 0.1%.

EXAMPLE 4

Preparation of milk chocolate

| | |
|---|---|
| Lactitol (crystalline, anhydrous) | 492 g |
| Cocoa butter | 222 g |
| Cocoa mass | 140 g |
| Milk powder | 110 g |
| Butter fat | 30 g |
| Lecithin | 3.8 g |
| Salt | 2.0 g |
| Vanillin | 0.2 g |

The lactitol, cocoa mass, milk powder, salt, vanillin and part of the mixture of cocoa butter and butter fat were mixed for 15 minutes in a Hermann Linden Z-blade mixer at 30°–40° C. The particle size of the mass was comminuted in a Lehmann three roller refiner in two-step rolling, the rolling pressures being 50/60 and 80/100. The mass was mixed for 15 minutes at 30°–40° C. between the rolling steps and thereafter. The remaining mixture of fats was added to the mass in these mixing steps. The final mixing, i.e. conching of the chocolate mass was carried out in a Friwessa mini conche at 50° C. for 18 hours with a speed of 4.5. Part of the lecithin was added at the beginning of the conching step to improve the mixability of the mass. The remainder of the lecithin was mixed into the mass at the end of the conching step. Chocolate masses were also prepared with a conching temperature of 40° C. or 60° C.

The viscosity of the conched chocolate mass was measured (Haake RV 12 Viscometer) according to the OICC method; furthermore, the yield value was calculated. Comparative tests were conducted using lactitol monohydrate or lactitol dihydrate instead of anhydrous lactitol. With a lactitol dihydrate mass, all of the lecithin had to be added thereinto already prior to the conching step on account of the fact that it had a more rigid structure than the other masses. A conching temperature above 40° C. could not be used, since at a higher temperature conching was not technically possible on account of the texture of the mass.

The viscosity and yield values have been presented in the Table below.

TABLE

Viscosity and yield value of milk chocolate masses after conching

| Sweetener | Conching temperature | Viscosity Poise | Yield value Dyne/cm$^2$ |
| --- | --- | --- | --- |
| Lactitol (crystalline, anhydrous) | 50 | 15.4 | 84 |
|  | 60 | 15.1 | 73 |
| Lactitol monohydrate | 50 | 20.6 | 70 |
|  | 60 | 25.3 | 48 |
| Lactitol dihydrate | 40 | 136.6 | 362 |

On account of its lower viscosity, chocolate mass manufactured using crystalline anhydrous lactitol was easier to treat further into products than lactitol monohydrate or dihydrate masses.

EXAMPLE 5

In the hard sweet tests performed, the products manufactured using lactitol of the invention were shown to be more stable than those manufactured using the reference compounds.

REFERENCE EXAMPLE

Anhydration of lactitol dihydrate

The preparation of lactitol anhydride by drying dihydrate was studied. Lactitol dihydrate had been recrystallized from water and dried with a drum drier at 30° C. with air. The lactitol dihydrate had a melting point of 72.5°–74.5° C., a water content of 9.4%, a lactitol content of 100% on dry matter and a crystal size of about 0.90 mm.

TEST 1

Lactitol dihydrate was stored for 5 days in an incubator at 60° C. A powdery substance having 2.1% of water was obtained. In DSC measuring (heating rate 2° C./min.), a small endothermic peak at 123° C., a small exothermic peak at 126° C. and a strong endothermic melting peak at 152° C. were detected. No trace of melting was found in the melting range of dihydrate.

TEST 2

Lactitol dihydrate was introduced into an incubator at 25° C., and the temperature was raised 0.5° C. per minute to 85° C., at which temperature the crystals were stored for another 16 hours. The resultant substance was a fully anhydrous powder which did not melt at 85° C. In DSC measuring (heating rate 2° C./ min.), a single strong endothermic melting peak was detected at 152° C.

TEST 3

Lactitol dihydrate was introduced into a DSC apparatus at 25° C., and the temperature was raised 0.5° C. per minute to 85° C., at which temperature the crystals were stored for another two hours. The resultant substance was a nearly anhydrous powder which did not melt at 85° C. In DSC measuring (heating rate 2° C./min.), only an endothermic region between 120° C. and 152° C. was detected (the most pronounced point was at 149° C.; this was obviously a result of the removal of residual water from the melt).

In the tests set out hereinabove, "lactitol anhydride" was produced which is known to be highly hygroscopic (European Patent Application No. 0231543, 1986). Thus it is evident that Wolfrom et al. (1938) referred to previously actually crystallized impure tetraedric dihydrate which turned into lactitol anhydride during the determination of the melting point.

We claim:

1. A process for preparing crystalline anhydrous lactitol having unit cell constants a=7.614 Å, b=10.757 Å, c=9.370 Å and β=108.2°, a melting point of 149° C. to 152° C., a water content below 0.5% and a lactitol content of more than 99%, by crystallizing from an aqueous solution which contains not less than 70% of lactitol on dry matter, characterized by bringing the aqueous lactitol solution to supersaturation in regard to lactitol, and subjecting the solution to crystallization conditions at a temperature range of 70° C. to 100° C., by evaporating the solution and/or lowering the temperature under simultaneous stirring, whereupon crystalline anhydrous lactitol is crystallized, wherein said resulting crystalline anhydrous lactitol absorbs less than about 0.1% of water at about 25° C. when the relative humidity is less than about 50%.

2. The process according to claim 1, characterized by evaporating the aqueous solution of lactitol to a concentration of 80–95% by weight and seeding the supersaturated solution at a temperature within the range 70°–100° C. spontaneously or by adding seed crystals, optionally evaporating further or adding solution, within the temperature range 70°–100° C. to increase the crystal content, and cooling the resultant mixture to a temperature ranging from 70° C. to 90° C., followed by separating the anhydrous lactitol crystals from the mother liquor, and optionally washing and drying.

3. The process according to claim 1, characterized by evaporating the aqueous solution of lactitol to a concentration of 85–95% by weight and seeding the supersaturated solution by adding seed crystals in a temperature range 80°–100° C., and cooling the mixture slowly to a temperature ranging from 70° C. to 90° C., and separating the anhydrous lactitol crystals from the mother liquor, and optionally washing and drying.

4. A process for preparing crystalline anhydrous lactitol of claim 1, wherein said aqueous solution contains not less than 90% of lactitol on dry matter.

5. A method for sweetening food comprising the steps of adding to said food a crystalline anhydrous lactitol belonging to the monoclinic crystal system and having unit cell constant a=7.61 Å, b=10.757 Å, c=9.37 Å, and β=108.2° and a melting point of 149° C. to 152° C., a water content below 0.5% and a lactitol content of more than 99%, and obtaining food sweetened with said crystalline lactitol, wherein said lactitol absorbs less than about 0.1% of water at about 25° C. when the relative humidity is less than about 50%.

6. The method of claim 5, wherein said food is a hard sweet.

7. The method of claim 5, wherein said food is chocolate.

* * * * *